May 13, 1958 F. MEILLAND Plant Pat. 1,700
ROSE PLANT
Filed Sept. 30, 1957
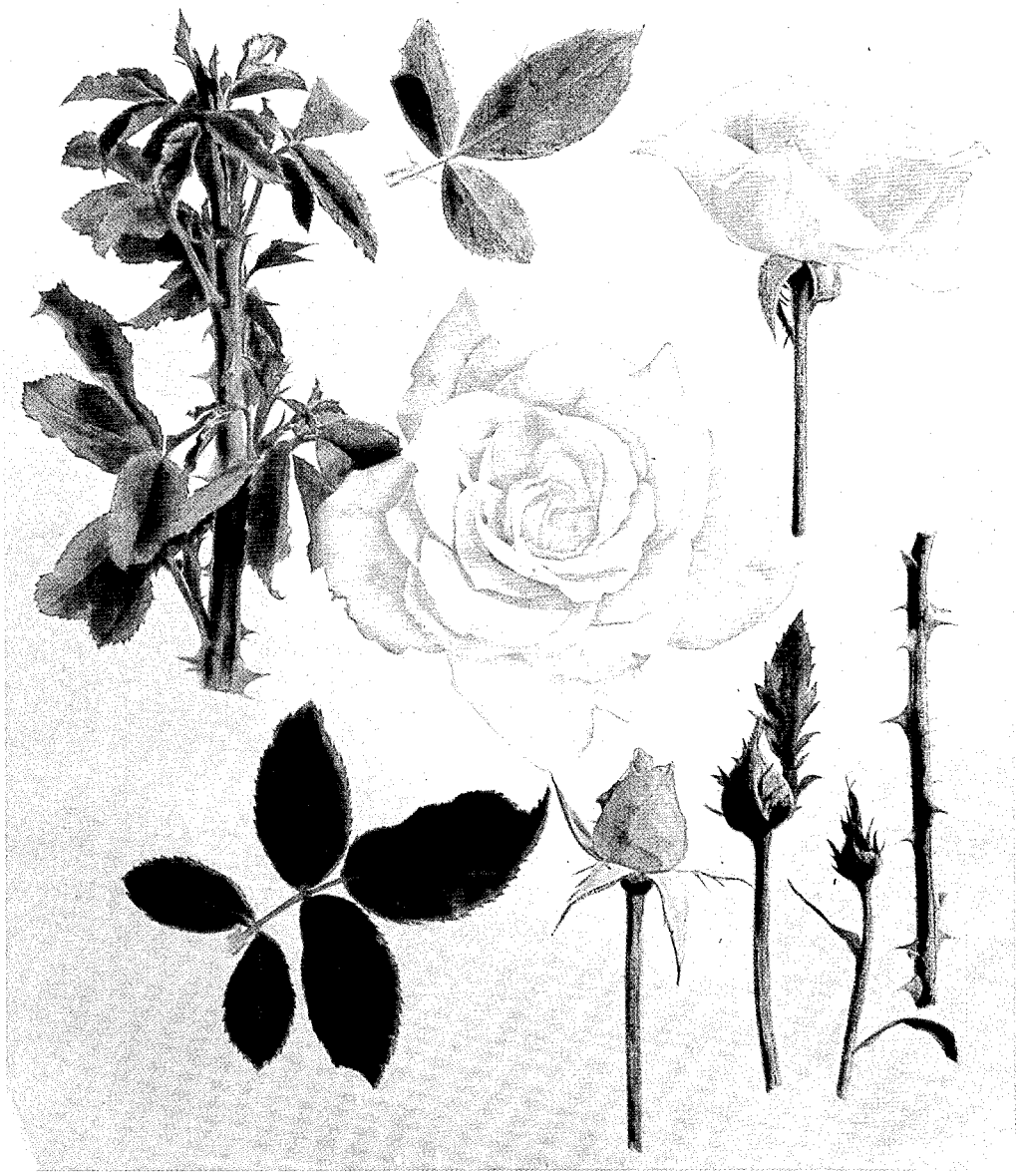
Inventor.
Francis Meilland
By: Robbs & Robb
Attorneys.

United States Patent Office

Plant Pat. 1,700
Patented May 13, 1958

1,700

ROSE PLANT

Francis Meilland, Cap Azura, Cap d'Antibes, Alpes Maritimes, France, assignor to The Conard-Pyle Company, West Grove, Pa., a corporation of Pennsylvania Application September 30, 1957, Serial No. 687,315

1 Claim. (Cl. 47—61)

The present invention relates to a new and distinct variety of rose plant of the hybrid tea class, which was originated by me by crossing an unnamed, undisseminated and unpatented seedling derived from "Independence," known in Europe as "Kordes' Sondermeldung" (U. S. Plant Patent No. 1,036) × "Happiness," known in Europe as "Rouge Meilland" (U. S. Plant Patent No. 911) with the variety "Better Times" (U. S. Plant Patent No. 23).

The primary objective of this breeding was to produce a new and improved rose variety which combines the freedom of growth and the orange-red flower color of "Independence" with the excellent flower form of "Happiness" and the growth and stem characteristics of both "Happiness" and "Better Times," and with the ability to grow and bloom in the greenhouse for cut flower purposes as is characteristic of "Better Times." These objectives were fully achieved, as evidenced by the following unique and desirable combination of characteristics which are outstanding in the new variety, and which distinguishes the same from its parents, as well as from all other varieties of which I am aware:

(1) A relatively tall, vigorous and free habit of growth, with stems of good cutting length;

(2) A marked increase in floriferousness, as compared with that of its parents;

(3) Excellence of form of the open flowers, which are of very double type;

(4) A distinctive and unusually clear and bright Delft Rose general color tonality of the flowers, which is well maintained throughout the life of the blooms; and (5) The good substance and long-lasting quality of the flower petals.

Asexual reproduction of the new variety by both budding and grafting, as performed in France, as well as at West Grove, Pennsylvania, U. S. A. and Richmond, Indiana, U. S. A., shows that the foregoing characteristics and distinctions come true to form and are established and transmitted through succeeding propagations.

The accompanying drawing shows typical specimens of the vegetative growth and flowers of the new variety in different stages of development and as depicted in color as nearly true as it is reasonably possible to make the same in a color illustration of this character.

The following is a detailed description of the new variety, with color terminology in accordance with the Horticultural Colour Chart of the Royal Horticultural Society, except where general color terms of ordinary dictionary significance are obvious:

Type: Hardy; bush; greenhouse and outdoor; seedling; for cut flowers and for garden decoration.

Class: Hybrid tea.

Breeding: Seedling.

*Seed parent.*—An unnamed and undisseminated seedling of "Independence" × "Happiness."

*Pollen parent.*—"Better Times."

Propagation: Holds its distinguishing characteristics through succeeding propagations by both budding and grafting.

*Flower*

Locality where grown and observed: West Grove, Pennsylvania, and Richmond, Indiana, U. S. A.

Flowers borne: Usually singly to stem; on stems of normal strength and medium length.

Quantity of bloom: Abundant, both outdoors and in greenhouse.

Continuity: Continuous.

Fragrance: Slight. Nature—musk.

Bud:

*Peduncle.*—Medium length; medium caliper; erect; stiff; rough; with numerous hairs of Oxblood Red, Plate 00823/3 color. Color—Lettuce Green, Plate 861/3, overlaid with Oxblood Red, Plate 00283/3 where exposed to sun.

*Before calyx breaks.*—Size—medium. Form—medium length; ovoid; with a conspicuous neck; with foliaceous appendages on the surface of the bud; with slender, bristle-like foliaceous parts extending beyond the tip of the bud equal to ¼ or more of its length.

*As calyx breaks.*—Color—Scarlet, Plate 19, with areas of Maroon, Plate 1030 where calyx first separates.

*As first petal opens.*—Size—medium large. Form—medium length; broadly ovoid. Color: outside—Delft Rose, Plate 020, sometimes blotched with Maroon, Plate 1030, and with point of attachment Sap Green, Plate 62/2; inside—Vermilion, Plate 18/1, with point of attachment Fern Green, Plate 0862/3.

*Opening.*—Opens up well.

Bloom:

*Size (when fully open).*—Medium large; from 4 to 4½ inches.

*Petalage.*—Very double; from 65 to 80 petals; arranged regularly.

*Form.*—Full cup-shaped at first, but becoming full-flat; petals being at first loosely rolled outward and remaining loosely rolled outward through maturity.

Petals:

*Texture.*—Medium thickness; leathery.

*Appearance.*—Inside—velvety. Outside—velvety.

*Shape.*—Outer petals—obovate; scalloped; generally no notches. Intermediate petals—obovate; scalloped; generally no notches. Inner petals—obovate; irregular; generally no notches.

This description of a newly opened flower was made from a rose grown outdoors in the month of August at West Grove, Pennsylvania, U. S. A.:

*Color.*—Outer petal: outside surface—Rose Madder, Plate 23/1, sometimes with blotches of Maroon, Plate 1030, with point of attachment Pod Green, Plate 061/1; inside surface—Delft Rose, Plate 020, with point of attachment Chartreuse Green, Plate 663/1, and with basal margin Rose Opal, Plate 022. Intermediate petal: outside surface—Rose Madder, Plate 23/1, with point of attachment Pod Green, Plate 061/1; inside surface—Delft Rose, Plate 020 at outer margin, shading to Rose Opal, Plate 022, with point of attachment Chartreuse Green, Plate 663/1. Inner petal: outside surface—Carmine, Plate 21/1, often with a streak of Magenta, Plate 27 along midrib; inside surface—Scarlet, Plate 19/1, with point of attachment Chartreuse Green, Plate 663/1.

This description was made from a rose that was open for three days outdoors in the month of August at West Grove, Pennsylvania, U. S. A.:

*Color.*—Outer petal: outside surface—Spinel Pink, Plate 0625, shading to Spirea Red, Plate 025/2, with basal area Rose Pink, Plate 427, and with point of attachment Pod Green, Plate 061/1; inside surface—Rose Opal, Plate 022/1, shading to Neyron Rose, Plate 623/1 towards base, with basal area Neyron Rose, Plate 623/3, and with point of attachment Chartreuse Green, Plate 663/3. Inner petal: outside surface—Spirea Red, Plate 025/2, with basal area Rose Pink, Plate 427, usually with a streak of Magenta Rose, Plate 027/1 running longitudinally through petal, and with point of attachment Pod Green, Plate 061/1; inside surface—Rose Opal, Plate 022/1, shading to Neyron Rose, Plate 623/1 over basal quarter of petal, with point of attachment Chartreuse Green, Plate 663/2.

*General color effect.*—Newly opened flower—Delft Rose, Plate 020/1, with areas of Vermilion, Plate 18/1 appearing when rose is viewed as a whole. Three-days open—Carmine, Plate 21/1 where petals are exposed to sun, with general color appearing between Rose Madder, Plate 23/1 and Rose Madder, Plate 23/2.

*Behaviour.*—Drop off cleanly.

*Flower longevity.*—On bush in garden—4 days in August. Cut roses grown outdoors and kept at living room temperatures—4 days in August.

*Reproductive organs*

Stamens: Medium number; arranged regularly about pistils.

Filaments: Many; most with anthers; medium length. Color—Uranium Green, Plate 63/3, usually tinged with Neyron Rose, Plate 623/1.

Anthers: All open at once; medium size; occasionally an anther fused with a petaloid. Color—Indian Yellow, Plate 6.

Pollen: Moderate. Color—gold.

Pistils: Medium number.

Styles: Uneven; medium length; medium caliper; bunched.

Stigma: Color—Primrose Yellow, Plate 601/1.

Ovaries: Some protruding from receptacle.

Hips: None.

Sepals: Permanent; spear-shaped.

Seeds: None.

*Plant*

Foliage:

*Leaves.*—Compound of 5 or 7 leaflets; from normal abundance to abundant; medium size; leathery.

*Leaflets.*—Shape—oval. Apex—acuminate. Base—obtuse. Margin—simply serrate.

*Color.*—Mature: upper surface—Spinach Green, Plate 0960/1; under surface—Willow Green, Plate 000862/1. Young: upper surface—slightly darker than Maroon, Plate 1030; under surface—near Oxblood Red, Plate 00823, with a gray cast.

*Rachis (the supporting stem of the compound leaf).*—Medium caliper, Upper side—grooved; hairy. Under side—sparsely prickley.

*Stipules.*—Medium length; medium width; with points of medium length turning out at an angle of more than 45°.

*Disease resistance.*—Comparable to that of the average variety grown under the same cultural conditions at West Grove, Pennsylvania, U. S. A.

Growth:

*Habit.*—Bushy; upright; much-branched.

*Growth.*—Vigorous.

*Canes.*—Medium caliper.

*Main stems.*—Color—Lettuce Green, Plate 861. Prickles—several; color—Orange Buff, Plate 507/2. Hairs—none.

*Branches.*—Color—Lettuce Green, Plate 861. Prickles—several; color—Orange Buff, Plate 507/2, often overlaid with Spinel Pink, Plate 0625. Hairs—few; color—reddish.

*New shoots.*—Color—Oxblood Red, Plate 00823/3. Prickles—several; color—Oxblood Red, Plate 00823/3. Hairs—few; color—reddish.

I claim:

A new and distinct variety of rose plant of the hybrid tea class, substantially as herein shown and described, characterized particularly as to novelty by its relatively tall, vigorous and free habit of growth, its flowering stems of good cutting length, its floriferousness, its very double blooms and their good form when open, the clear, bright Delft Rose general color tonality of its blooms and their habit of maintaining their color throughout their life, and the good substance and longlasting quality of the flower petals.

No references cited.